(12) United States Patent
Yu

(10) Patent No.: US 9,370,482 B1
(45) Date of Patent: Jun. 21, 2016

(54) METHOD OF INCORPORATING ADDITIVES TO SHAPED POROUS MONOCOMPONENT BIOPOLYMER FIBERS DURING FIBER ORIENTING STEP

(76) Inventor: Harrison Yu, Midlothian, VA (US)

( * ) Notice: Subject to any disclaimer, the term of this patent is extended or adjusted under 35 U.S.C. 154(b) by 254 days.

(21) Appl. No.: 13/199,761

(22) Filed: Sep. 9, 2011

(51) Int. Cl.
*A61L 17/14* (2006.01)
*A61K 9/00* (2006.01)

(52) U.S. Cl.
CPC ............... *A61K 9/0024* (2013.01); *A61L 17/14* (2013.01)

(58) Field of Classification Search
CPC ...................................... A61L 17/145
USPC ............ 427/2.1, 2.31; 424/422, 426; 442/334
See application file for complete search history.

(56) References Cited

U.S. PATENT DOCUMENTS

| | | | |
|---|---|---|---|
| 4,043,331 A | 8/1977 | Martin et al. | |
| 4,087,246 A | 5/1978 | Mares et al. | |
| 4,537,738 A | 8/1985 | Holmes | |
| 4,820,460 A | 4/1989 | Repetti et al. | |
| 5,057,368 A | 10/1991 | Largman et al. | |
| 5,625,029 A | 4/1997 | Hubbs et al. | |
| 5,858,395 A | 1/1999 | Shikinami | |
| 5,939,467 A | 8/1999 | Wnuk et al. | |
| 5,973,100 A | 10/1999 | Asrar et al. | |
| 6,514,515 B1 | 2/2003 | Williams | |
| 6,592,892 B1 | 7/2003 | Williams | |
| 6,610,764 B1 | 8/2003 | Martin et al. | |
| 6,685,957 B1 | 2/2004 | Bezemer et al. | |
| 6,746,685 B2 | 6/2004 | Williams | |
| 6,814,911 B2 * | 11/2004 | Ward et al. .................... 264/121 |
| 6,825,285 B2 | 11/2004 | Autran et al. | |
| 6,905,987 B2 | 6/2005 | Noda et al. | |
| 6,913,784 B2 | 7/2005 | Xue et al. | |
| 7,098,292 B2 | 8/2006 | Zhao et al. | |
| 7,268,205 B2 | 9/2007 | Williams et al. | |
| 7,301,000 B2 | 11/2007 | Satkowski et al. | |
| 7,442,223 B2 | 10/2008 | Rohrbach et al. | |
| 7,517,381 B2 | 4/2009 | Rohrbach et al. | |
| 7,641,825 B2 | 1/2010 | Rizk | |
| 7,666,946 B2 | 2/2010 | Brake et al. | |
| 7,888,275 B2 | 2/2011 | Ward et al. | |
| 8,003,719 B2 | 8/2011 | Padwa | |
| 8,034,270 B2 | 10/2011 | Martin et al. | |
| 8,039,237 B2 | 10/2011 | Martin et al. | |
| 8,048,446 B2 | 11/2011 | Lelkes et al. | |
| 8,071,382 B2 | 12/2011 | Bae et al. | |
| 8,084,125 B2 | 12/2011 | Rizk | |
| 8,157,918 B2 | 4/2012 | Becker et al. | |
| 8,287,909 B2 | 10/2012 | Martin et al. | |
| 8,408,216 B2 | 4/2013 | Luan et al. | |
| 2004/0234576 A1* | 11/2004 | Martin et al. .................. 424/426 |
| 2009/0162276 A1* | 6/2009 | Martin ..................... A61L 15/26 424/1.11 |
| 2010/0267867 A1 | 10/2010 | Cygan et al. | |

OTHER PUBLICATIONS

Simon F Williams, David P Martin, Daniel M Horowitz, Oliver P Peoples, International Journal of Biological Macromolecules, Jun. 1999, 111, vol. 25, Issues 1-3, Elsevier.
J. Cobntbekt, R.H. Mabchessault, Journal of Molecular Biology, Nov. 28, 1972, 735, vol. 71, Issue 3, Elsevier.
Mitsuru Yokouchi, Yozo Chatani, Hiroyuki Tadokoro and Hisaya Tani, Polymer Journal, 1974, 248, vol. 6 , No. 3, The Society of Polymer Science, Japan.

* cited by examiner

*Primary Examiner* — Cachet Sellman

(57) ABSTRACT

Biopolymers, and natural and bio additives are process-sensitive materials, prefer minimized steps and mild parameters. With all of prior achievements in making products from biopolymers, biopolymers have less than 1% of total polymers global usage after over a century of growth. A process is disclosed to make fibers from biopolymers and to incorporate the fibers with additives during the fiber forming steps via minimized steps and mild parameters.

6 Claims, No Drawings

US 9,370,482 B1

METHOD OF INCORPORATING ADDITIVES TO SHAPED POROUS MONOCOMPONENT BIOPOLYMER FIBERS DURING FIBER ORIENTING STEP

FIELD

The present invention generally relates to the field of making fibers from biopolymers and additives.

BACKGROUND

There are long remained challenges in making products from biopolymers. Biopolymers are process-sensitive materials. Biopolymers, natural and bio additives prefer minimized steps and mild parameters. Prior art in making products from biopolymers use extended steps and harsh parameters. Prior art modifies biopolymers through conventional mixing, blending, compounding, and compositing steps. These extended steps, harsh parameters, and modifications can significantly and substantially change intrinsic properties of biopolymers, and natural and bio additives. Intrinsic properties of these materials can be completely changed. And these materials can be converted into chemical materials. Performance/price ratios of products from biopolymers via prior art are significantly and substantially decreased. Directly due to these intrinsic property changes, biopolymers have less than 1% of total polymers global usage after over a century of growth.

Businesses in biopolymers have already made plenty of improving achievements from prior art in new raw materials, new blend/mixture/compound/composite materials, new processes, new performance features of products, and pioneering applications into new markets since 1900s. The manufacturing costs of biopolymers have been substantially reduced since 1990s. However, all of prior achievements have to make products from biopolymers and additives through extended steps and harsh parameters. There are long felt and unsatisfied needs on making products from biopolymers and additives via minimized steps and mild parameters.

Polymers with normal relaxation times have their intrinsic process challenges on incorporating these polymers with natural and bio additives during product forming steps. Extended steps and harsh parameters have to be used to keep molecular chains, functional groups, and pendant groups of these polymers activated and oriented. Unfortunately, these extended steps and harsh parameters result in significantly and substantially intrinsic property changes on natural and bio additives. These intrinsic property changes make it impossible to incorporate activated and oriented molecular chains, functional groups, and pendant groups of polymers having normal relaxation times with natural and bio additives.

PRIOR ART

U.S. Pat. No. 8,287,909 Summary and US 20090162276 Summary form fibers from polyhydroxyalkanoates (PHAs) with high velocity air at a temperature of 100-300° C. Biopolymers are process-sensitive materials, preferring minimized steps and mild parameters. U.S. Pat. No. 9,125,719 Table 1 and US 20040234576 Table 1 mention that molecular weight changes were at a range from 30 to 50% during making fibers from PHAs.

U.S. Pat. No. 6,814,911 Abstract incorporates an additive into porous fibers from polymers having normal relaxation times by heating the formed fibers with a heating medium, whereby the heating medium simultaneously carries the additive material into the fibers. The incorporation of fibers with bioactive additives, bio additives, flavors, prophylactic additives, therapeutic additives, hygiene, fragrance, and natural drugs prefer minimized steps, and mild carriers and environments.

Polymers with normal relaxation times have their intrinsic process challenges on in-situ incorporating these polymers with natural and bio additives during product forming steps. Extended steps and harsh parameters have to be used to keep molecular chains, functional groups, and pendant groups of these polymers activated and oriented. Unfortunately, these extended steps and harsh parameters result in significantly and substantially intrinsic property changes of natural and bio additives. These intrinsic property changes make it impossible to incorporate activated and oriented molecular chains, functional groups, and pendant groups of polymers having normal relaxation times with natural and bio additives.

U.S. Pat. No. 6,685,957 first clarifies that often, the methods used to prepare porous structures are not suitable for incorporation of labile protein and other bioactive compounds, due to the high temperatures used, exposure to organic solvents, or the need for removal of the porogens. Then this patent itself teaches a method of electrospinning porous fibers incorporated with labile proteins and other bioactive compounds, exposed to organic solvents during preparing solution step, and high electrical voltage during the fiber making step. Biopolymers are process-sensitive materials, preferring minimized steps and mild parameters.

US 20100267867 describes poor melt strength caused by less than ideal biopolyesters and process conditions. US 20100267867 and U.S. Pat. No. 7,666,946 teach blend of one or more biopolyesters with one or more acrylic copolymers can improve process performance of biopolyesters. Unfortunately, intrinsic properties of biopolyesters may be no longer available due to various interactions between biopolyesters and acrylic copolymers during the blending step. U.S. Pat. No. 6,905,987 mentions that bicomponent shaped porous fibers are made from polyhydroxyalkanoates (PHAs)/polylactic acid (PLA) polymer or copolymer blends. PHAs, PLA polymer or copolymer, and other additives are most preferably mixed by extruders and spun into bicomponent fibers. After the fiber is formed, the fiber may further be treated or the bonded fabric can be treated with desired additives. Intrinsic properties of biopolyesters could be lost due to the interactions among various biopolyesters during these mixing steps.

SUMMARY

Biopolymers demonstrate long relaxation times during and after processing. This phenomenon reveals molecular chains, functional groups, and pendant groups of biopolymers are still activated and oriented even under mild energy and temperature environments, and have certain macro scale performances. Molecular chains, functional groups, and pendant groups of biopolymers are still activated and oriented even at a pressure of about 100 kPa and a temperature of about 20° C. environment after activation and orientation. These performances provide biopolymers a unique and intrinsic process opportunity. Additives can be fully incorporated and interacted with activated and oriented molecular chains, functional groups, and pendant groups of biopolymers at a pressure of about 100 kPa and a temperature of about 20° C. environment during product forming steps.

Biopolymers, and natural and bio additives are process-sensitive materials. These materials prefer minimized process steps and mild parameters. By exploring and reducing this opportunity, a process for making fibers from biopolymers and incorporating the activated and oriented molecular structures of biopolymers with additive via minimized steps and mild parameters during the fiber forming steps has been invented. This process satisfies two long felt needs. Intrinsic properties of biopolymers and natural and bio additives can be reserved. Natural and bio additives can be fully incorporated and interacted with activated and oriented molecular chains, functional groups, and pendant groups of biopolymers via minimized steps and mild parameters during the fiber forming steps. Via this invention, Natural and bio additives are encapsulated by molecular structures and material structures of biopolymers.

Products made from this process comprise medical devices, drug devices, flavor devices, nutrient devices, fragrance devices, separation devices, filtration devices, collection devices, hold devices, or control release devices.

This process can be used via merging with conventional tools, biopolymers, additives, and process steps and parameters by an ordinary skilled person in the art. Processes of making fibers, porous fibers, and shaped porous fibers from biopolymers, methods of the incorporation of additives, and processes of making fibers into final products through further downstream process steps are all standard ones.

DEFINITION

"Intrinsic properties" as generally used herein means properties derived from formulation of monomers, functional groups, and pendant groups.

"Relaxation Time" as generally used herein means the time for:
1. a molecular structure of a biopolymer to reach to its new equilibrium states after activation and orientation.
   a. The molecular structure of a biopolymer herein comprises molecular chains, functional groups, and pendant groups, etc. of a biopolymer molecule.
2. a material structure of a biopolymer to reach to its new equilibrium states after activation and orientation.
   a. The material structure of a biopolymer herein comprises both amorphous structures and crystal structures.

"Long Relaxation Time" as generally used herein means compared with ordinary polymers either fossil ones or chemical ones, biopolymers have longer relaxation times.
1. The molecular structure of a biopolymer herein has longer relaxation times.
   a. Each of the molecular chains, the functional groups, and the pendant groups, etc. of a biopolymer molecule herein has longer relaxation times.
2. The material structure of a biopolymer has longer relaxation times.
   a. The crystal structure of a biopolymer herein has longer relaxation time—low crystallization rate.

"Mild Parameters" as generally used herein comprise mild process parameters, mild carrying medium parameters, and mild forming product environment parameters.

Materials

Materials with this invention broadly include any polymers with long relaxation times after activation and orientation. Preferable polymers comprise biopolymers, biopolyesters, and polyhydroxyalkanoates. Biopolymers include poly(lactide)s; poly(lactide-co-glycolide)s; poly(lactic acid)s; poly(lactic acid-co-glycolic acid)s; polyhydroxyalkanoates; poly-3-hydroxybutyrates; copolymer of 3-hydroxybutyrate with 3-hydroxyvalerates; P4HB copolymers; synthetically or biologically prepared polyesters; chitins; chitosans; hyaluronic acid and derivatives thereof; hydrophilic or water soluble biopolymers.

Polyhydroxyalkanoates are used in embodiments of this invention. Poly (3-hydroxybutyrate-co-3-hydroxyvalerate)s with 3-20 mol % 3-hydroxyvalerate are used in examples of this invention to enable an ordinary skilled person in the art how to merge this invention with conventional tools, materials, machinery, and process steps and parameters.

Additives include performance agents, adsorbents, absorbents, surfactants, plasticizers, aging agents, blowing agents, swelling agents, nucleating agents, nucleophiles and electrophiles consisting of alcohols, acids, and amine groups, hydrophilic agents, hydrophobic, prophylactic agents, therapeutic agents, diagnostic agents, fragrance, flavors, nutrients, hygiene, bioactive, and bio additives.

Adsorbents, absorbents, prophylactic agents, therapeutic agents, diagnostic agents, flavors, fragrance, nutrients, hygiene, and bioactive additives are used in embodiments of this invention. Menthol and molecular sieves are used in examples of this invention to show an ordinary skilled person in the art how to merge this invention with conventional tools, materials, machinery, and process steps and parameters.

EMBODIMENT

The embodiment of this invention is only used to illustrate the principles of the process for making fibers from biopolymers and incorporating the fibers with additives via minimized steps and mild parameters during the fiber forming steps. It will be apparent to an ordinary skilled person in the art that different modifications and variations of this process can be made without departing from the scope or spirit of this invention. As clarified above, these inventive concepts can be broadly developed into various products made from any polymers with long relaxation times after their activation and orientation steps through either fluid methods or hot melt methods.

In one embodiment is provided fibers are formed from biopolymers having long relaxation times via minimized steps and mild parameters. Via minimized steps and mild parameters intrinsic properties of biopolymers are reserved and directly turned into performances of the fibers. Biopolymers comprise poly(lactide)s; poly(lactide-co-glycolide)s; poly(lactic acid)s; poly(lactic acid-co-glycolic acid)s; polyhydroxyalkanoates; poly-3-hydroxybutyrates; copolymer of 3-hydroxybutyrate with 3-hydroxyvalerates; P4HB copolymers; synthetically or biologically prepared polyesters; chitin; chitosan; hyaluronic acid and derivative thereof; hydrophilic or water soluble biopolymers. The fibers can be further made into various devices of medicine, drug, flavor, nutrient, fragrance, separation, hygiene, filtration, collection, hold, or control release via further downstream process steps.

In one embodiment is provided activated and oriented molecular main chains, functional groups, and pendant groups of biopolymers, and fibers from the biopolymers are incorporated with additives in a form of solid or fluid via minimized steps and mild parameters during the fiber forming steps. The additives comprise adsorbents, absorbents, reinforcements, blowing additives, surfactants, plasticizers, aging additives, nucleating additives, nucleophiles and electrophiles consisting of alcohols, acids, and amine groups, hydrophilic, hydrophobic, prophylactic additives, therapeutic additives, diagnostic additives, fragrance, flavors, nutrients, hygiene, bioactive, bio additives, or natural drugs. Molecular chains, functional groups, and pendant groups of biopolymers are all still in activated and oriented states under said mild parameters. Natural and bio additives can be incorporated and interacted with activated and oriented molecular chains, functional groups, and pendant groups of biopolymers via minimized steps and mild parameters during the fiber forming steps. The additives are encapsulated by both molecular structures and material structures of said biopolymers under said mild parameters. Via minimized steps and mild parameters intrinsic properties of the additives are reserved and directly turned into performances of the incorporated fibers. The incorporated fibers can be further made into various devices of medicine, drug, flavor, nutrient, fragrance, separation, hygiene, filtration, collection, hold, or control release via further downstream process steps.

In one embodiment is provided fibers are formed from biopolymers having long relaxation times via minimized steps and mild parameters, and activated and oriented molecular main chains, functional groups, and pendant groups of biopolymers, and fibers from the biopolymers are incorporated and interacted with additives in a form of solid or fluid via minimized steps and mild parameters during the fiber forming steps. Via minimized steps and mild parameters intrinsic properties of the biopolymers and the additives are reserved and directly turned into performances of the incorporated fibers. Molecular chains, functional groups, and pendant groups of biopolymers are all still in activated and oriented states under said mild parameters. Natural and bio additives can be incorporated and interacted with activated and oriented molecular chains, functional groups, and pendant groups of biopolymers during the fiber forming steps. The additives are encapsulated by both molecular structures and material structures of said biopolymers under said mild parameters. The incorporated fibers can be further made into various devices of medicine, drug, flavor, nutrient, fragrance, separation, hygiene, filtration, collection, hold, or control release via further downstream process steps.

The activating and spinning steps and parameters, and tools before the forming steps with the embodiment of this invention are conventional steps and tools to those skilled in the art. Tools and methods for the incorporation of activated and oriented molecular main chains, functional groups, and pendant groups of biopolymers, and fibers from biopolymers with additives in a form of solid or fluid are all conventional ones to those skilled in the art. Further downstream forming steps and tools after the incorporation of additives are conventional ones to those skilled in the art.

In one embodiment is provided fiber is formed from biopolymers having long relaxation times, and activated and oriented molecular main chains, functional groups, and pendant groups of biopolymers, and fiber forming and orienting from biopolymers are in-situ incorporated with additives in a form of solid or fluid via minimized steps and a pressure of about 100 kPa and a temperature of from about 150° C. to about 20° C. environment during the fiber forming steps.

In one embodiment is provided fiber is formed from biopolymers having long relaxation times, and activated and oriented molecular main chains, functional groups, and pendant groups of biopolymers, and fiber forming and orienting from biopolymers are in-situ incorporated with additives in a form of solid or fluid via minimized steps and a pressure of about 100 kPa and a temperature of about 20° C. environment during the fiber forming steps.

EXAMPLES

Poly (3-hydroxybutyrate-co-3-hydroxyvalerate)s with 3-20 mol % 3-hydroxyvalerate (PHBVs) are fed into an extruder and heated for about 2 minutes at a temperature from about 150° C. to about 200° C. The PHBV melt is extruded and spun into a shaped fiber preform from a die with a single shaped hole spinneret having a diameter from 0.5 mm to 1.5 mm. These activating and spinning steps before the forming steps are conventional steps.

The shaped preform is stretched into the oriented and shaped fibers under a pressure of 100 kPa and at a temperature from about 150° C. to about 20° C. environment. The fibers are collected by a winder having a speed from 50 m/min to 100 m/min. The collected fibers have diameters from about 10 microns to about 400 microns.

The fibers are incorporated with nanoscale and microscale additives along the die to the winder under a pressure of 100 kPa and at a temperature from about 150° C. to about 20° C. environment.

Methods and tools of the incorporation comprises blowing, spraying or injecting the molecular main chains, functional groups, and pendant groups of PHBV and the fibers with fluid additives, or impregnating or injecting the molecular main chains, functional groups, and pendant groups of PHBV and the fibers with solid additives. Methods and apparatuses for the incorporation of molecular structures of PHBV and material structures of fibers with additives are conventional ones.

The fibers can be further made into fiber products through downstream process steps. Further downstream forming steps and tools are conventional steps.

Molecular chains, functional groups, and pendant groups of PHBV and the fibers are sprayed with menthols during the fiber forming steps. Methods and apparatuses for spraying these Molecular chains, functional groups, and pendant groups and fibers with menthol are apparent to those skilled in the art.

Menthols are encapsulated in microscale and nanoscale molecular sieve carrier particles. The fibers may be impregnated with these particles during the fiber forming steps. Methods and apparatuses for the impregnation of the fibers with these particles are apparent to those skilled in the art.

A shaped porous PHA fiber can be incorporated with a metal agent and made into a cigarette tow filter in vapor and gas selective filtration. Said filter is used to selectively bind to unsaturated hydrocarbons such as 1, 3-butadiene. The binding can occur by insertion of a metal atom of the metal reagent into a C—H bond or a C—C bond of the gaseous component. A metal reagent comprises nanometer or micrometer size clusters of a transition metal or alloy containing a transition metal. The transition metal can be incorporated in an intermetallic compound such as titanium aluminide or iron aluminide. The metal clusters can be incorporated in or on a support material such as silica gel, or porous carbon or a zeolite.

What is claimed is:

1. A method for forming shaped polyhydroxyalkanoate biopolymer fibers having additives included therein comprising:

Heating, melting, extruding, and spinning a polyhydroxyalkanoate having pendant groups thereon into shaped polyhydroxyalkanoate biopolymer fiber preforms by melt spinning, Orienting and forming said shaped polyhydroxyalkanoate biopolymer fiber preforms into shaped, porous polyhydroxyalkanoate biopolymer fibers using a winder collector in a manner such that angles formed between molecular chains and said pendant groups of said polyhydroxyalkanoate and relaxation times of said molecular chains and said pendant groups during said orienting and shaping are sufficient to allow incorporation of additives into said shaped, porous polyhydroxyalkanoate biopolymer fibers, During said orienting step, incorporating additives with said fibers, said molecular chains, and said pendant groups, Said orienting and forming steps do not comprise exposure of said polyhydroxyalkanoate and said additives to temperatures, organic solvents, or electrical voltages which cause a decrease in the molecular weight of said polyhydroxyalkanoate and said additives.

2. The method of claim 1, wherein said heating, melting and extruding is conducted at 150 to 200° C.

3. The method of claim 1, wherein said additives are incorporated with said fibers, said molecular chains, and said pendant groups by blowing, spraying, or injecting fluid additive agents during said orienting step.

4. The method of claim 1, wherein said additives are incorporated with said fibers, said molecular chains, and said pendant groups by impregnating or injecting solid additive agents during said orienting step.

5. The method of claim 1, wherein said additives are selected from the group consisting of comprising bioactive additives, bio additives, flavors, nutrients, fragrances, and drugs.

6. The method of claim 1, wherein said shaped, porous polyhydroxyalkanoate biopolymer fibers are further formed into a medical device for surgical, drug delivery, therapeutic, or diagnostic applications.

* * * * *